(12) United States Patent
Girton

(10) Patent No.: US 6,770,086 B1
(45) Date of Patent: Aug. 3, 2004

(54) STENT COVERING FORMED OF POROUS POLYTETRAFLOUROETHYLENE

(75) Inventor: Timothy Samuel Girton, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 117 days.

(21) Appl. No.: 09/704,494

(22) Filed: Nov. 2, 2000

(51) Int. Cl.⁷ ............................................... A61F 2/06
(52) U.S. Cl. .................... 623/1.13; 623/1.39; 623/1.49
(58) Field of Search .............................. 623/1.13, 1.39, 623/1.4, 1.49, 901, 1.46, 1.44, 1.45

(56) References Cited

U.S. PATENT DOCUMENTS

| | | | |
|---|---|---|---|
| 4,533,369 A | * 8/1985 | Okita ........................... 55/158 |
| 4,657,544 A | 4/1987 | Pinchuk | |
| 4,764,560 A | * 8/1988 | Mitchell ..................... 524/506 |
| 4,945,125 A | 7/1990 | Dillon et al. | |
| 5,066,683 A | 11/1991 | Dillon et al. | |
| 5,157,058 A | 10/1992 | Dillon et al. | |
| 5,466,509 A | 11/1995 | Kowligi et al. | |
| 5,639,278 A | * 6/1997 | Dereume et al. ............... 623/1 |
| 5,641,373 A | 6/1997 | Shannon et al. | |
| 5,693,085 A | 12/1997 | Buirge et al. | |
| 5,700,285 A | 12/1997 | Myers et al. | |
| 5,735,892 A | 4/1998 | Myers et al. | |
| 5,741,326 A | 4/1998 | Solovay | |
| 5,747,128 A | 5/1998 | Campbell et al. | |
| 5,749,880 A | 5/1998 | Banas et al. | |
| 5,769,884 A | 6/1998 | Solovay | |
| 5,782,904 A | 7/1998 | White et al. | |
| 5,788,626 A | 8/1998 | Thompson | |
| 5,810,870 A | 9/1998 | Myers et al. | |
| 5,824,046 A | 10/1998 | Smith et al. | |
| 5,843,161 A | 12/1998 | Solovay | |
| 5,843,173 A | 12/1998 | Shannon et al. | |
| 5,925,074 A | 7/1999 | Gingras et al. | |
| 5,925,075 A | 7/1999 | Myers et al. | |
| 5,928,279 A | 7/1999 | Shannon et al. | |
| 5,928,280 A | 7/1999 | Hansen et al. | |
| 5,948,191 A | 9/1999 | Solovay | |
| 5,980,923 A | 11/1999 | Dillon | |
| 6,004,348 A | 12/1999 | Banas et al. | |
| 6,010,529 A | 1/2000 | Herweck et al. | |
| 6,022,902 A | 2/2000 | Koontz | |
| 6,053,943 A | * 4/2000 | Edwin et al. ............... 623/1.25 |
| 6,143,675 A | * 11/2000 | McCollam et al. ......... 442/221 |
| 6,156,064 A | * 12/2000 | Chouinard .................. 623/1.44 |
| 6,235,377 B1 | * 5/2001 | Dillon et al. ............... 428/212 |
| 6,245,099 B1 | * 6/2001 | Edwin et al. ............... 623/1.13 |

FOREIGN PATENT DOCUMENTS

| | | | | |
|---|---|---|---|---|
| JP | 06116774 A | * 10/1992 | ........... C25B/11/00 |
| WO | WO 87/02996 | 5/1987 | |
| WO | WO 96/00103 | 1/1996 | |
| WO | WO 98/38947 | 9/1998 | |
| WO | WO 00/30564 | 6/2000 | |

OTHER PUBLICATIONS

Kipke et al., Pub. Date Oct. 18, 2001, US2001/0031978 A1, Method for Forming an Endovascular Occlusion.*

* cited by examiner

Primary Examiner—Bruce Snow
Assistant Examiner—Cheryl Miller
(74) Attorney, Agent, or Firm—Hoffman & Baron, LLP

(57) ABSTRACT

A porous polytetrafluoroethylene substrate is used in an endoprosthesis device. An elongate radially expandable tubular stent is also included with the porous PTFE substrate, and form the endoprosthetic device. A method of making the porous polytetrafluoroethylene entails a novel method including siloxane in PTFE and thereafter removing the siloxane to form the porous structure. The PTFE structure does not have nodes and fibrils.

6 Claims, 7 Drawing Sheets

STENT COVERING FORMED OF POROUS POLYTETRAFLOUROETHYLENE

FIELD OF THE INVENTION

The present invention relates to an endoprosthesis device or intraluminal device, in particular a stent, having a covering comprising porous polytetrafluoroethylene formed by removing the siloxane from an interpenetrating network of polytetrafluoroethylene and siloxane, and to a method of making the endoprosthesis device. The stent covering can be applied on the exterior surface of the stent, on the interior surface of the stent, or both, at a thickness of as low as about 15 microns.

BACKGROUND OF THE INVENTION

Endoprosthesis devices including stents, stent-grafts, grafts, vena cava filters, balloon catheters, and so forth, are placed or implanted within various body vessels for the treatment of various diseases. One particular type of an endoprosthesis device is the stent. A stent is implanted within a vessel for the treatment of stenoses, strictures, or aneurysms in the blood vessels. The devices are implanted within the vascular system to reinforce diseased, partially occluded, weakened or abnormally dilated sections of the blood vessel. Stents are often employed after angioplasty to prevent, restenosis of a diseased blood vessel. While stents are most notably used in blood vessels, they have also been implanted in other bodily vessels including urinary tracts and bile ducts to reinforce and prevent neoplastic growth.

Stents are typically longitudinal tubular devices formed of biocompatible materials and come in a variety of construction types, and are often expandable in nature. Many if not all of the materials used for stents involve metal or carbon fiber materials which are highly electro-positive and are bio-active. Since stents tend to be used under conditions were they are counteracting disease processes, supporting healing processes, or guarding against stenosis of a passage, bio-activity, which may encourage undesirable or poorly regulated growth processes, or lead to clot formation, should be avoided.

Coating of the stent can keep the stent from directly contacting surrounding tissue or fluids, and thus can theoretically protect against unwanted electrochemically induced tissue reactions.

In the field of expandable stents, a further problem arises due to the fact that many stent constructions involve structures that have numerous apertures or spaces between various strands or structural elements of the stent such as those structures that are filamentous, wire-like, or of a tubular nature in which various openings have been cut or etched into the stent. With these constructions, tissue may grow through the openings of the stent. Furthermore, the stent itself may provoke a foreign body reaction and be both a stimulus for and a framework supporting, proliferative tissue growth, resulting, for example, in scar tissue or restenosis of the very region it is placed to control.

One approach to this drawback is to provide a coating, liner, cover or both, for the stent which prevents the healing or diseased layer of tissue from directly contacting the stent, or from passing through the stent in any way. Such liners may be formed, for example, of porous polytetrafluoroethylene (PTFE) which allows the passage of fluids and vital materials while serving as a barrier to tissue growth. However, when applying such a construction, a further difficulty which may arise is that the layer or sleeve of polymer must be attached to the stent for example, by staples or sutures at one end, or is prone to developing loose pockets or folds which might accumulate organic matter or lead to sepsis or unusual growth. Also, the necessarily thin liner material may detach or degrade. The risk of loose or unattached liner material is particularly great for constructions which utilize poorly adherent polymers, such as PTFE, or structures which seek to combine an expandable stent of stiff material, which changes both its dimension and its shape, with a dissimilar liner or shell.

One method for overcoming these problems is found in U.S. Pat. No. 6,010,529 in which tube of polymeric material, e.g. expanded polytetrafluoroethylene (PTFE), is passed through the interior of a stent body and is turned back upon itself over the stent to form a cuff. The assembly is then heated and the outer layer contacts and coalesces with the inner layer, closely surrounding the stent body within a folded envelope having a continuous and seamless end. Porosity is imparted to the PTFE by previous stretching or expansion the material.

Another type of covered stent which permits radial expansion is shown in WO 96/00103. As shown and described therein, a metallic expandable stent includes an outer covering of ePTFE. The ePTFE cover exhibits suitable expansion capabilities so as to enable the cover to expand upon expansion of the underlying stent. A polytetrafluoroethylene/lubricant blend may be extruded into a tube and the tube heated to remove the lubricant. Then, in order to impart the expandable characteristics to the ePTFE cover during formation of the ePTFE cover material, the ePTFE must undergo successive processing steps of expanding the material, sintering the material, radially dilating the material and resintering the dilated material, a procedure that is quite process intensive. The device described therefore requires precise manufacturing techniques and is extremely processing sensitive. Careful processing of the material forming the cover is required in order for the cover to exhibit sufficient expansion capabilities.

U.S. Pat. No. 5,824,046 describes a composite intraluminal device, in particular an elongate radially expandable tubular stent having an interior luminal surface and an opposed exterior surface extending along a longitudinal stent axis. A stent cover is formed of unsintered ePTFE which is expandable.

There remains a need in the art to provide a stent with a cover material that is sufficiently expandable, has the requisite barrier properties and yet allows the passage of fluids and vital materials, without requiring extensive processing procedures and is thus easily manufactured and applied to the stent.

SUMMARY OF THE INVENTION

The present invention relates to a method of forming porous polytetrafluoroethylene (PTFE) without having to stretch or expand the material, and to a radially expandable endoprosthesis device covered with the solid but expandable polymer covering comprising the porous PTFE material obtained using the method of the present invention. The porous PTFE covering physically isolates the endoprosthesis from surrounding blood and tissue.

Specifically, the porous PTFE is prepared by extracting siloxane from an interpenetrating network (IPN) of PTFE and siloxane, leaving behind a porous PTFE structure without having to expand and stretch the PTFE. Consequently, the PTFE material used in the endoprosthesis device coverings of the present invention is not expanded PTFE, but it is porous.

In one embodiment the end of the prosthesis device of the present invention includes an elongate radially expandable tubular stent having an interior surface and in exterior surface extending along a longitudinal stent access. The expandable tubular stent has a stent cover on said interior surface, exterior surface or both, the cover being formed of a porous polytetrafluoroethylene. The porous polytetrafluoroethylene cover is a non-stretched porous structure, the non-stretched structure lacking note and viable structure.

In particular, the present invention relates to a radially expandable stent for use in treating stenoses wherein the stent is covered with an expandable polymer covering comprising the porous PTFE prepared according to the present invention that physically isolates the stent from surrounding blood and tissue.

DETAILED DESCRIPTIONS OF THE PREFERRED EMBODIMENTS

The present invention provides a covered stent which may be implanted intraluminally within a body vessel and disposed adjacent an occluded, weakened or otherwise damaged portion of the vessel so as to hold the vessel open. The covered stent is typically delivered intraluminally via a balloon catheter. The device is delivered in a compressed condition and once properly positioned may be deployed by radial expansion. The most common form of deploying the intraluminal device is by balloon expansion, however, the present invention may also be deployed by use of a self-expanding stent.

Figure 1:
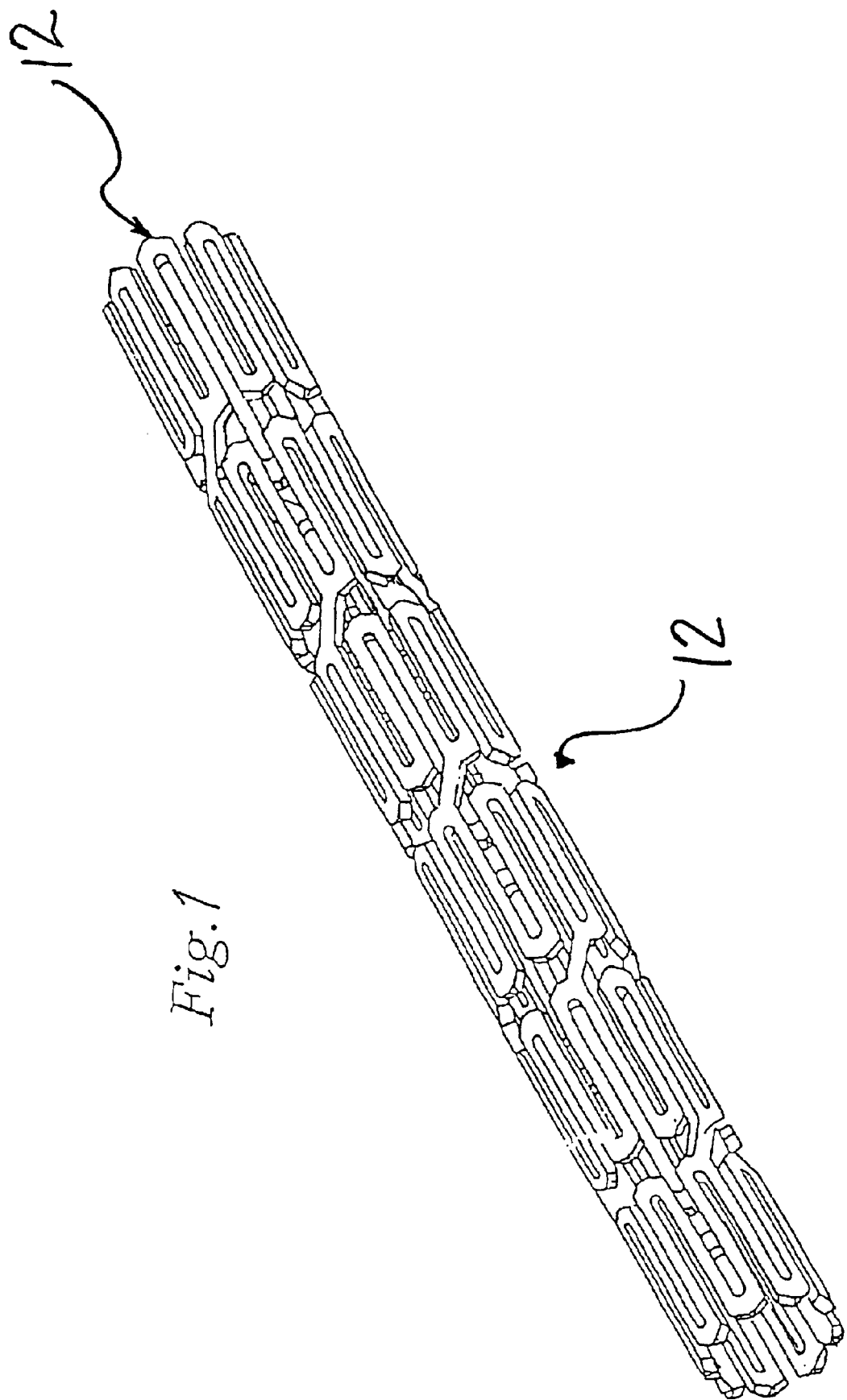
FIG. 1 is a perspective view of one type of intraluminal device that may be used in the present invention.
Figure 2:
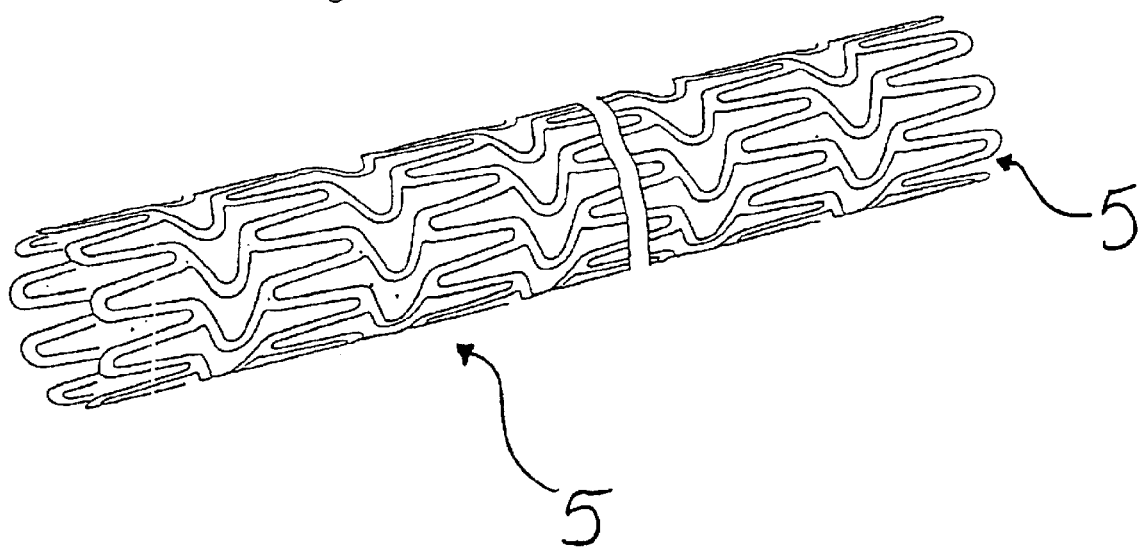
FIG. 2 is a perspective view of a different intraluminal device which may be used in the present invention.

FIG. 1 illustrates an intraluminal device in the form of a stent 12. FIG. 2 illustrates an intraluminal device in the form of a stent 5 having a different construction than that shown in FIG. 1.

Figure 3:
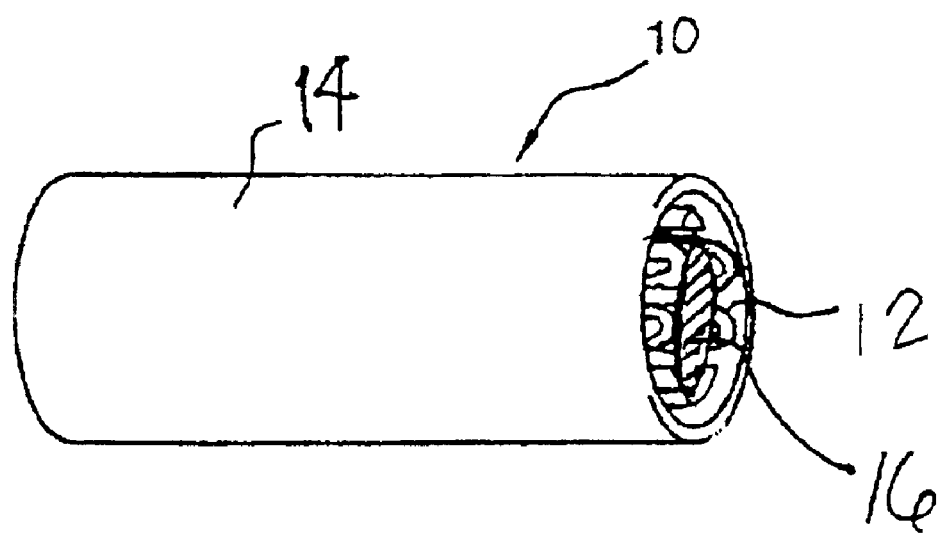
FIG. 3 is a perspective view of the intraluminal device of FIG. 1 illustrating the device having a polytetrafluoroethylene cover on both the inner and outer surface of the device.
Figure 5:
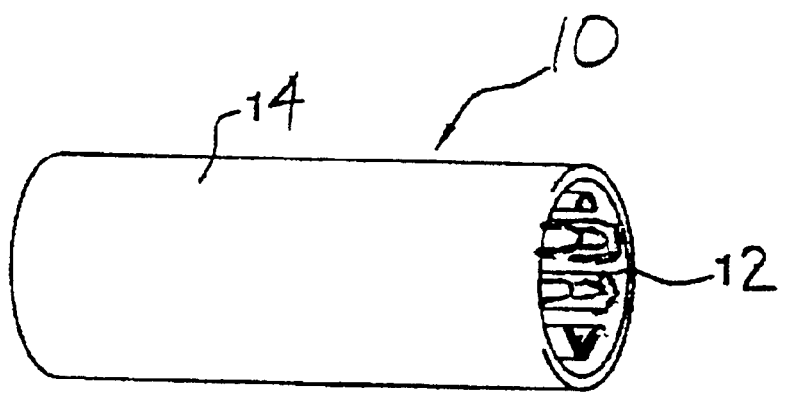
FIG. 5 is the same intraluminal device as in FIG. 3 illustrating only the outer surface cover.
Figure 6:
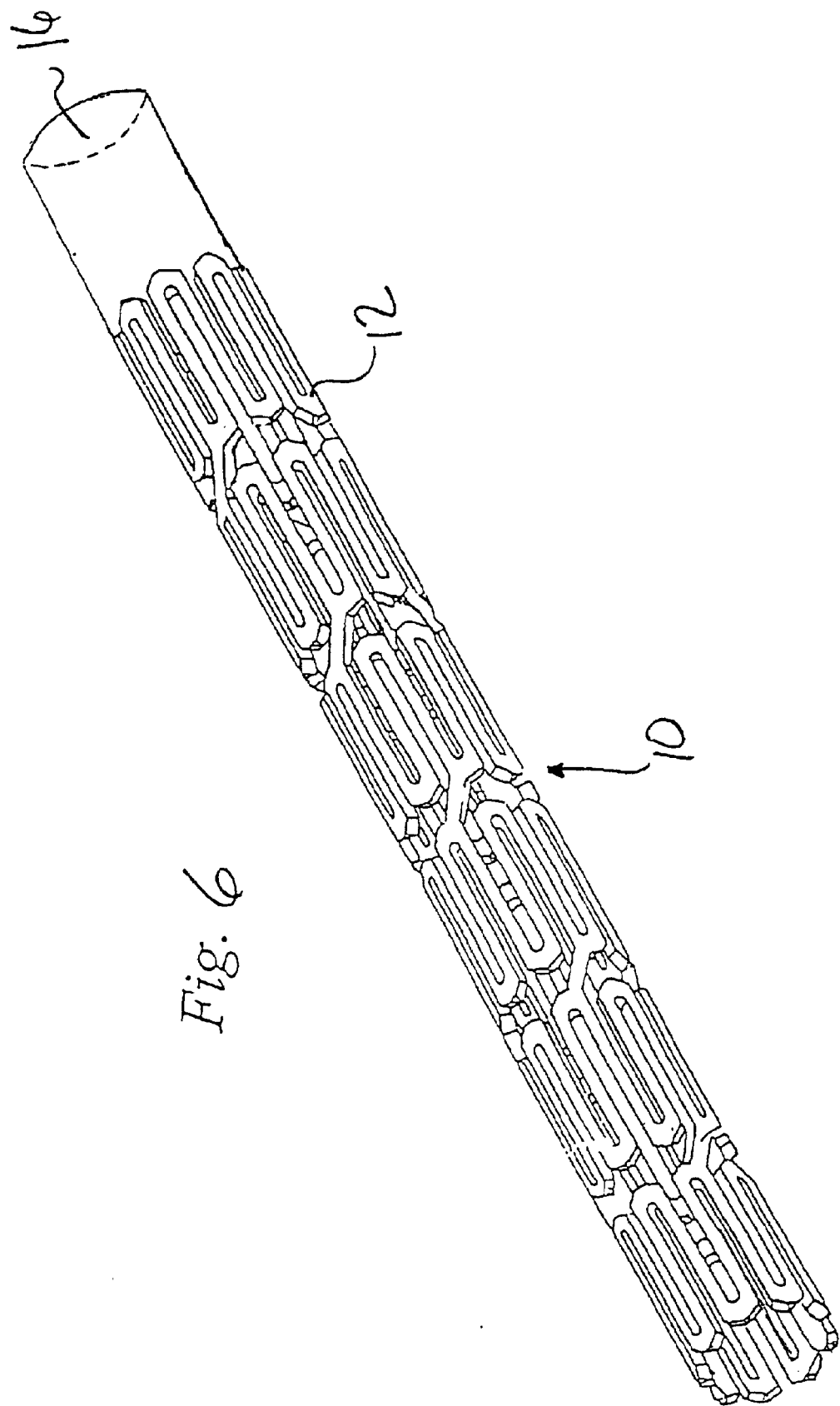
FIG. 6 is the same intraluminal device as in FIG. 3 with the exception that only a liner or inner surface cover is shown.
Figure 7:
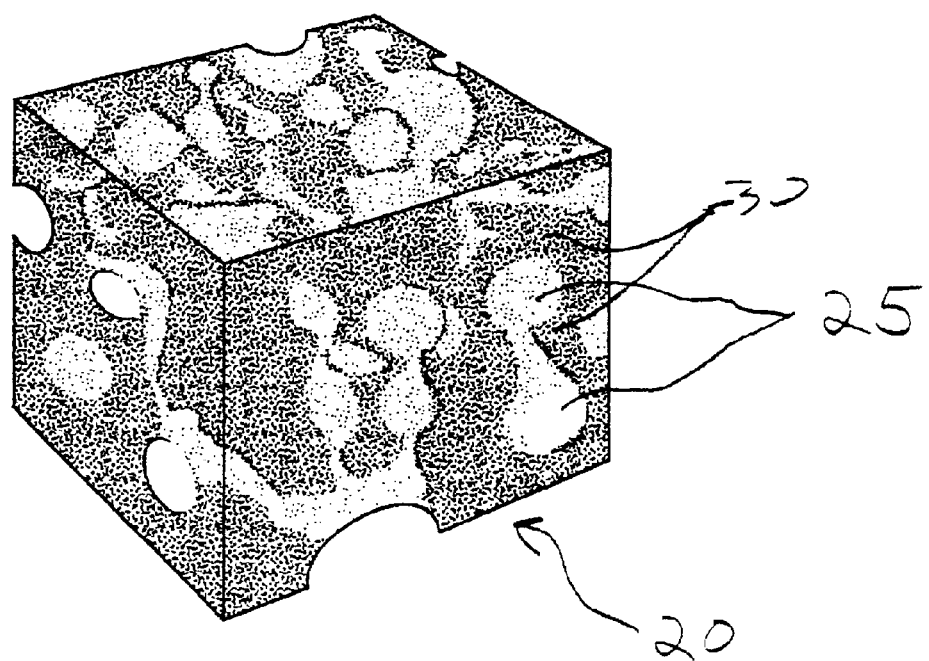
FIG. 7 is a cross-section of the porous PTFE material of the present invention.

FIG. 3 illustrates generally at 10 an intraluminal device in the form of a stent 12 as shown in FIG. 1 having a cover 14 on the outer surface of the stent 12 and liner 16 on the inner surface, both of which may be of the porous structure shown below in FIG. 7. The stent may optionally have only a cover 14 as shown in FIG. 5, or only a liner 16 as shown in FIG. 6, or both as shown in FIG. 3. In a preferred embodiment, the stent has both a cover 14 and a liner 16. The liner, cover, or both, will be referred to hereinafter collectively as a cover or covering. The cover provides an effective barrier about the stent 12 preventing excessive cell or tissue ingrowth or thrombus formation through the expanded wall of the stent 12.

Figure 4:
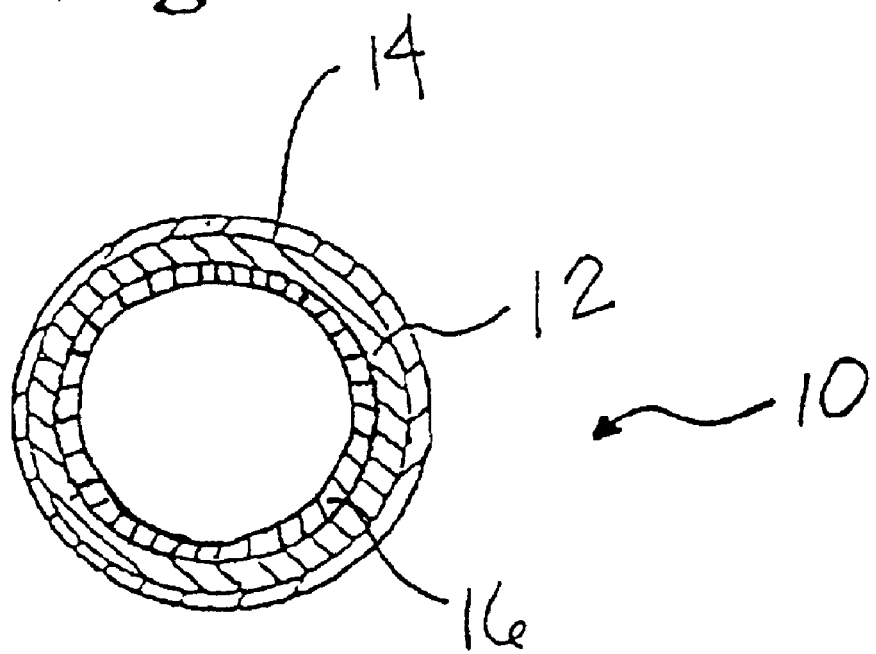
FIG. 4 is a cross-sectional view of the same intraluminal device shown in FIG. 3.

FIG. 4 is a cross-sectional view of the same device as shown in FIG. 3 with a cover 14 and a liner 16 around stent 12.

FIG. 1 is a more detailed illustration of stent 12 and shows generally an elongate tube. The body of stent 12 defines an opposed interior surface 11 and an exterior surface 13 and is formed of a generally open configuration having a plurality of openings or passages provided for longitudinal flexibility of the stent as well as permitting the stent to be radially expanded once deployed in the body lumen. Both the interior surface 11 and the exterior surface 13 may have the porous PTFE covering of the present invention. On the interior surface the covering is referred to as the liner 12 as shown in FIG. 1 and on the exterior surface it is referred to as a cover 14 as shown in FIG. 1.

While the figures illustrate a particular construction of stent 10, one of skill in the art would recognize that the porous PTFE covering material as described by the present invention would find utility in any stent configuration, and in particular the open stent configurations.

Stent 12 may be employed in combination with a cover 14 or liner 16 but is preferably employed with both. The cover 14 may be applied over the tubular stent 12 so as to fully circumferentially surround the stent 12, while the liner 16 is applied inside and through the stent 12 so that the stent 12 fully circumferentially surrounds the liner 16.

The porous polytetrafluoroethylene (PTFE) material useful herein is first obtained in the form of an interpenetrating network of PTFE and siloxane, in particular, polydimethylsiloxane. The silicone is then extracted from the IPN using either thermal or chemical means. The removal of the silicone leaves behind a porous PTFE structure. A particular material for use herein is Silon®, an interpenetrating polymer network (IPN) of polytetrafluoroethylene (PTFE) and polydimethylsiloxane (silicone) supplied by Bio Med Sciences, Inc. located in Bethlehem, Pa. Such IPN polymer networks are described in U.S. Pat No. 6,022,902 incorporated by reference herein in its entirety. In this patent, Silon® is described as a breathable, hydrophobic polysiloxane membrane reinforced with poly(tetrafluoroethylene).

The removal of the siloxane from the IPN leaves behind a porous PTFE structure without having to go through the added steps of stretching or expanding the PTFE in order to obtain the porous structure. Quite obviously, this simplifies the manufacturing process by decreasing the number of steps required, and also increases efficiency. Typically, porous PTFE requires the expanding and stretching steps in order to achieve the porous structure. FIG. 7 illustrates generally at 20 a porous PTFE structure after removal of the siloxane. The removal of the siloxane leaves behind the porous structure wherein voids or pockets of air 25, are found intermeshed in between pockets of PTFE 30.

Figure 8:
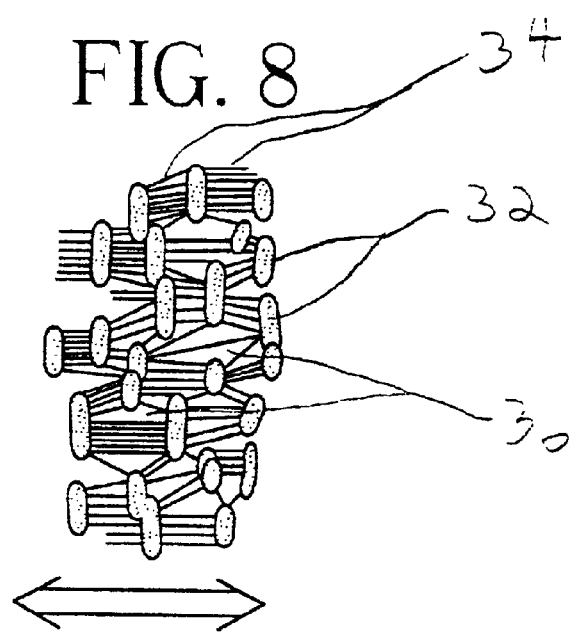
FIG. 8 is a schematic representation of ePTFE prior art.

The novel porous PTFE structure produced by the present inventive process is quite different from the porous structure produced by PTFE which has been stretched, or expanded. Typically, PTFE which has been stretched, or ePTFE has a node and fibril structure as seen in FIG. 8. After stretching, the ePTFE possesses nodes 32 connected to fibrils 34. In between the nodes and fibrils are pores 36.

Removing the siloxane from the IPN of siloxane/PTFE through the use of heat involves heating the IPN structure to temperatures of between about 300° C. and about 390° C. Chemical removal of the siloxane may be accomplished using a compound selected from the group consisting of toluene, heptane, chloroform.

Sintering is typically accomplished at or above the crystalline melting point of PTFE. Sintering is synonymous with recrystallization. It refers to the bonding of particles in a mass by molecular (or atomic) attraction in the solid state through the application of heat below the melting point of the polymer. Sintering causes the strengthening of the powder mass and normally results in densification and often recrystallization.

A PTFE tube may be extruded as a tube from an extrusion device, or extruded as a film and subsequently wrapped into a tube. Extrusion techniques of PTFE are well known in the art.

As discussed above, the stent may be covered on the interior surface 11 of the stent 12, the exterior surface 13 of the stent 12, or both. Preferably, the stent 12 is covered on both the interior 11 and the exterior 13 surfaces of the stent 12. Having the entire surface of the stent 12 covered with the porous PTFE of the present invention provides an effective barrier about the stent 12 preventing excessive cell or tissue growth, or thrombus formation through the expanded wall of a tubular stent 12.

In order for the covering of porous PTFE to function effectively in combination with an expandable stent, the material must exhibit sufficient expansion characteristics so as to enable a the stent cover to expand along with the radial expansion of the stent 10. If the covering material does not effectively expand with the stent, several problems can arise. The covering material may tear, and may even detach from the surface of the stent if improper or dissimilar expansion of the covering material occurs with the expansion of the stent.

In order to improve the adhesion, and further prevent detachment of the PTFE covering from the stent, the PTFE may be fused or welded around or to the metal stent. This may be accomplished either through a heating process and/or bonding process. If heating is utilized, typically the PTFE will be heated above its sintering temperature.

If an adhesive is utilized, preferably a biocompatible adhesive is used. Such adhesives are known to one of skill in the art and include, for example, polyurethanes, epoxies, cyanoacrylates, polyamides, polyimides, silicones, and so forth. Dispersions of PTFE or FEP (fluoroethylpropylene) may also be utilized. This list is not exclusive and is intended for illustrative purposes only, and is in no way intended as a limitation on the scope of the present invention. There is a vast number of adhesives that can be used for such applications, limited by their biocompatibility, and by their ability to bond to polymeric materials (e.g. PTFE) and metals, particularly in aqueous environments.

The covering material may also be assembled to the intraluminal device in more than one piece. Such a combination would require overlapping of sorts of the PTFE material, and subsequent fusion or adhesive bonding of the porous PTFE material to itself.

It is preferable, however, to utilize the porous PTFE covering in a continuous form such as a membrane or thin film. The porous PTFE (after removal of the siloxane), in the form of a membrane or a thin film, thus, preferably completely wraps the metal stent, thereby providing a barrier that physically isolates the stent from surrounding blood and tissue. This barrier further helps prevent healing or diseased layers of tissue from directly contacting the stent, or from passing through the stent in any way. The porous PTFE allows the passage of fluids and vital materials, however, while still serving as a barrier to tissue growth.

What is claimed is:

1. A method of covering an endoprosthesis device comprising the steps of:

providing an elongate radially expandable tubular stent;

providing a polytetrafluoroethylene having no node and fibril structure;

imparting porosity to said polytetrafluoroethylene by extracting siloxane from an interpenetrating network of siloxane and polytetrafluoroethylene;

forming a stent cover from said porous polytetrafluoroethylene; and applying said stent cover to an interior surface and exterior surface, or both of said stent wherein said stent cover extends along a longitudinal stent axis.

2. The method of claim 1 wherein said stent cover is applied to said interior surface and to said exterior surface of said stent.

3. The method of claim 1 wherein said stent cover is fixed to said stent using an adhesive.

4. The method of claim 3 wherein said adhesive is selected from the group consisting of polyurethanes, epoxies, cyanoacrylates, polyamides, polyimides, and silicones.

5. The method of claim 1 wherein said stent cover is fixed to said stent by a welding process, said welding process comprising heating the polytetrafluoroethylene stent cover to a temperature that is greater than the sintering temperature of the polytetrafluoroethylene.

6. The method of claim 1 wherein said siloxane is polydimethylsiloxane.

* * * * *